(12) United States Patent
Swisher et al.

(10) Patent No.: US 12,285,295 B2
(45) Date of Patent: *Apr. 29, 2025

(54) ULTRASOUND SYSTEM WITH A NEURAL NETWORK FOR PRODUCING IMAGES FROM UNDERSAMPLED ULTRASOUND DATA

(71) Applicant: KONINKLIJKE PHILIPS N.V., Eindhoven (NL)

(72) Inventors: Christine Menking Swisher, San Diego, CA (US); Jean-Luc Francois-Marie Robert, Cambridge, MA (US); Man Nguyen, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/581,848

(22) Filed: Feb. 20, 2024

(65) Prior Publication Data

US 2024/0225607 A1    Jul. 11, 2024

Related U.S. Application Data

(63) Continuation of application No. 16/975,929, filed as application No. PCT/EP2019/054402 on Feb. 22, 2019, now Pat. No. 11,957,515.

(Continued)

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/4444* (2013.01); *A61B 8/4494* (2013.01);
(Continued)

(58) Field of Classification Search
CPC ............................................ G06T 2207/30048
See application file for complete search history.

(56) References Cited

U.S. PATENT DOCUMENTS

2013/0310678 A1* 11/2013 Balbi ...................... A61B 5/055
600/443
2018/0075581 A1* 3/2018 Shi .......................... G06N 3/045

FOREIGN PATENT DOCUMENTS

WO    WO-0205208 A2 *  1/2002 ........... G06T 3/4007
WO    2017113205 A1    7/2017

OTHER PUBLICATIONS

Goodfellow, et al., "Generative Adversarial Nets", NIPS' 14 Proceedings of the 27th International Conference on Neural Information Processing Systems, vol. 2, Dec. 8, 2014, pp. 2672-2680.

(Continued)

*Primary Examiner* — Joseph M Santos Rodriguez
*Assistant Examiner* — Tommy T Ly (57) ABSTRACT

The present disclosure describes medical imaging systems and methods configured to generate medical images based on undersampled imaging data. The images may be generated by applying a neural network trained with samples of known fully sampled data and undersampled data derived from the known fully sampled data to a acquired sparsely sampled data. The training of the neural network may involve training adversarial generative network including a generator and a discriminator. The generator is trained with sets of known undersampled data until the generator is capable of generating estimated image data, which the classifier is incapable of differentiation as either real or fake, and the trained generator may then be applied to unknown undersampled data.

18 Claims, 8 Drawing Sheets

Related U.S. Application Data

(60) Provisional application No. 62/635,775, filed on Feb. 27, 2018.

(51) Int. Cl.
*G06N 3/04* (2023.01)
*G06N 3/08* (2023.01)

(52) U.S. Cl.
CPC .................. *G06N 3/04* (2013.01); *G06N 3/08* (2013.01); *G06T 2207/30048* (2013.01)

(56) References Cited

OTHER PUBLICATIONS

Hor, et al., "Generative Adversarial Networks for Ultrasound Compressed Sensing", Jun. 21, 2018, Retrieved from the Internet: URL:http://cs230.stanford.edu/files_winter2018/projects/6940402.pdf, pp. 1-6. (Abstract).
International Search Report and Written Opinion for International Application No. PCT/EP2019/054402, filed Feb. 22, 2019, 21 pages.
Perdios, et al., "A deep learning approach to ultrasound image recovery", 2017 IEEE International Ultrasonics Symposium, Sep. 2017, 4 pages.

\* cited by examiner

ULTRASOUND SYSTEM WITH A NEURAL NETWORK FOR PRODUCING IMAGES FROM UNDERSAMPLED ULTRASOUND DATA

RELATED APPLICATION

This application is a continuation application of U.S. patent application Ser. No. 16/975,929 filed on Aug. 26, 2020, which in turn is the U.S. National Phase application under 35 U.S.C. § 371 of International Application No. PCT/EP2019/054402, filed on Feb. 22, 2019, which claims the benefit of and priority to U.S. Provisional No. 62/635,775, filed Feb. 27, 2018, which is incorporated by reference.

TECHNICAL FIELD

The present disclosure pertains to ultrasound systems and methods for generating ultrasound images using undersampled ultrasound data. Particular implementations involve systems which implement and apply a neural network to produce an ultrasound image from undersampled ultrasound data.

BACKGROUND

In many imaging modalities, such as ultrasound imaging, there is a tradeoff between acquisition speed and image quality. Resolution and/or field of view size may be sacrificed in order to acquire real time or near real time images. For example, cardiac imaging may require a high frame rate in order to visualize movements of heart valves or muscle. However, if resolution is not adequate, the diagnostic value of the acquired images and/or cineloop may be limited.

Computational techniques for reconstructing ultrasound images from undersampled (also referred to as sparsely sampled or simply sparse) ultrasound data have been developed to attempt to increase frame rate and/or field of view while maintaining resolution. However, many of these techniques may excessively smooth images, reduce speckle information, and/or introduce artifacts. Some techniques for reconstructing images may be so computationally intensive that they cannot provide reconstructed images from undersampled data in real time or near real time, reducing their utility.

SUMMARY

The present disclosure describes systems and methods for generating ultrasound images using undersampled ultrasound data. Undersampling may occur in, but not limited to, the following situations, e.g., 1) the fast-time acquisition time, where the signal data points are sparsely sampled, 2) the spatial domain where only a subset of elements are used for image reconstruction, and/or 3) slow-time domain where low frame rate acquisition is applied on fast moving targets.

Reconstructing undersampled data, e.g., using techniques such as compressive sensing, may lead to unacceptably slow reconstruction times and artifacts such as speckle artifacts, whereas implementing a deep generative network on unknown sparsed data may lead to fake lesions and/or false normalization of lesions.

The present invention relates to systems and methods that may solve one or more of the above noted problems of unusable reconstruction times of traditional compressive sensing reconstruction techniques and introduction of artifacts and false data of existing generative networks. In some embodiments, these problems may be solved by obtaining known undersampled data and training a neural network (e.g., a generative adversarial network) using the known undersampled data. This may reinforce data consistency because a generative network can learn to correct the noise or aliasing artifacts of the true data from the non-uniform under sampling (as opposed to filling in missing data). The knowledge thus learned by the neural network may then be applied to unknown under sampled data.

As described herein, a neural network trained in accordance with the examples herein may simulate and/or reconstruct data missing or degraded from undersampling of a signal, thereby enabling the use of underasmpled ultrasound data for generating a quality image (e.g., a higher quality image than the data would natively allow) and/or shortening acquisition times. In some examples, the neural network may be a least a portion (or sub-network) of a deep generative network. For example, the neural network may implement one or more neural network models of an adversarial generative network. The one or more neural networks implemented in a system according to the examples herein may be applied to temporally and/or spatially undersampled ultrasound sensor data to output ultrasound images at higher frame rate and/or with improved image quality. For example, image data may be acquired at a relatively low frame rate (e.g., 20-40 Hz for 2D imaging and 2-10 Hz for 3D imaging) and the system and techniques described herein may generate and display the image data at frame rates two or three times faster than the acquisition rate. That is, the images generated for display may have a temporal resolution and appear as if they were captured with a faster frame rate than the low frame rate actually used.

As described herein, the one or more neural networks implemented in a system according to the examples herein may be trained using a generative adversarial approach. The network being trained may include a generator and a discriminator, which may be trained simultaneously. The generator may implement a generative classification model, while the discriminator may implement a discriminative classification model. The generator may be trained to generate (simulate or estimate) fully-sampled ultrasound images using known undersampled ultrasound image data (e.g., an image deliberately undersampled from a fully sampled image by removing some of the samples of the fully sampled image). The discriminator may be trained to classify data produced by the generator as either real or fake data. Once the generator is capable of producing an estimated fully-sampled image that can fool the discriminator, the generator may be implemented in a field-deployable system for generating ultrasound images (e.g., an imaging system or an analysis workstation) to produce ultrasound images from unknown undersampled data.

In some embodiments, a system for generating ultrasound images may include at least one storage device and at least one processor coupled to the storage device. The system may be programmed to, e.g., using executable instructions stored on at least one non-transitory computer readable medium coupled to the processor, to receive undersampled ultrasound data, modify, using at least one neural network, the undersampled ultrasound data to represent sufficiently-sampled ultrasound data, and generate an ultrasound image based on the modified ultrasound data. The neural network may be trained by providing a first ultrasound data set comprises sufficiently-sampled ultrasound data, reducing sampling of the first ultrasound data set to produce a second ultrasound data set with missing data, generating, by the one or more neural networks including the neural network, new data estimated to represent the missing data, producing a third ultrasound data set by modifying the second ultrasound data set to include the new data, classifying, by the one or more neural networks, the third ultrasound data set as real or fake, and adjusting activation rules for one or more nodes of the one or more neural networks based on an accuracy of the classifying.

In some embodiments, the neural network may include at least a portion, such the generative model, of a generative adversarial network and may be trained in accordance with any of the examples herein. For example, training the generative adversarial network may be include receiving a plurality of previously-acquired ultrasound images, each comprising an acquired sufficiently-sampled ultrasound dataset and reducing sampling of each of the sufficiently-sampled ultrasound datasets to produce respective generated sparse ultrasound datasets. The training of the neural network with training sets comprising pairs of acquired sufficiently-sampled and corresponding generated sparse ultrasound datasets may further include coupling the generated sparse ultrasound dataset of each pair to the generative model to produce a generated sufficiently-sampled ultrasound dataset, coupling the acquired sufficiently-sampled and the generated sufficiently-sampled ultrasound dataset of each pair to the discriminative model to classify the generated sufficiently-sampled ultrasound dataset as real or fake and to compute an error signal representative of accuracy of the classification, and adjusting one or more activation functions for respective one or more nodes of the discriminative model and the generative model, wherein the adjusting is configured to reduce the error signal.

Any of the methods described herein, or steps thereof, may be embodied in non-transitory computer-readable medium comprising executable instructions, which when executed may cause a processor of a medical imaging system to perform the method or steps embodied herein.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

There is typically a tradeoff between acquisition speed and image quality in ultrasound imaging. Image quality factors may include, but are not limited to, resolution, contrast, absence of artifacts, and scanning area/volume. A possible way to improve image quality for high acquisition speed is to apply a priori information on the imaged medium. In the past few years, compressive sensing techniques (CS) have been investigated. A priori information is implemented by enforcing sparsity. However, enforcing sparsity may create artifacts that remove real image characteristics in ultrasound images making it difficult to obtain simultaneously very high frame rates, contrast and resolution enhancements. Moreover, CS reconstruction algorithms are slow making them difficult for clinical use and often impossible to be deployed in real-time. Furthermore, CS is sensitive to the model used, and a mismatch between the model and actual data can reduce performance. Undersampling and reconstruction techniques other than CS may suffer from similar disadvantages.

Figure 1:
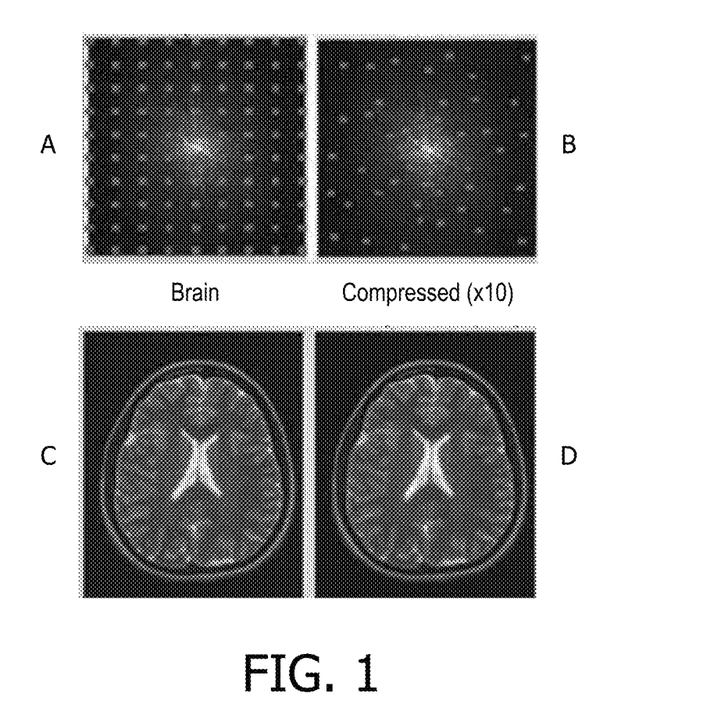
FIG. 1 shows example brain images constructed from regularly sampled data and undersampled data.

FIG. 1 shows example brain images constructed from regularly sampled data and undersampled data. Image A shows raw data with a regular sampling pattern overlaid. Image B shows the same raw data as image A with an undersampling pattern overlaid. The undersampling pattern in the example shown in image B is a nonuniform undersampling pattern that compresses the data by a factor of ten. Image C shows a high resolution brain image constructed from the data sampled by the regular sampling pattern shown in image A. Image D shows a brain image constructed from the data sampled by the undersampling pattern shown in image B. In the example shown in image D, a compressive sensing (CS) reconstruction algorithm was used. The CS reconstructed image is based on real underlying information. However, image D is smoothed compared to image C, which may be undesirable in some applications. Furthermore, the CS reconstruction process may be too slow to be implemented on an ultrasound imaging system for real time imaging.

Deep generative networks (DGNs), a family of neural networks, have be shown to simulate high quality data that cannot be distinguished from real data by human viewers. DGNs may be capable of generating images in real or near real time. However, real appearing data created with DGNs alone could produce incorrect medical diagnoses due to the creation of fake data, such as a fake lesion (e.g., false positive) or normalization of a malignant lesion (e.g., false negative). Known approaches for implementing a deep generative network include Variational Autoencoders (VAEs) and Generative Adversarial Networks (GANs). VAEs generally aim at maximizing the lower bound of the data log-likelihood while GANs aim at achieving an equilibrium between a generator and a discriminator. In some embodiments herein, a GAN modeling framework may be used to implement the neural network applied to undersampled data for producing a better-quality image than the undersampled data would otherwise permit. A GAN suitable for the current application may be implemented as described, for example by Goodfellow, Ian, Jean Pouget-Abadie, et al., in "Generative Adversarial Nets" published in *Advances in Neural Information Processing Systems* 27 (*NIPS* 2014), pages 2672-2680, which publication are incorporated herein by reference in its entirety for any purpose.

As will be described further below, systems and methods for reconstructing, using a neural network, a medical image from undersampled data may be used to produce a higher quality image than would otherwise be possible with existing techniques (e.g., using CS reconstruction or existing GAN approaches). The techniques described herein may be used to produce an image from a modified (by a machined trained algorithm) image data set that includes more information than the information in the starting dataset, which is generally referred to herein as undersampled data. The undersampling may be in the temporal or spatial domain. That is, the upsampling achieved by the neural network may be temporal e.g., to increase frame rate, or spatial, e.g., to produce a higher resolution image. A DGN such as one implementing a GAN algorithm or model, may be trained to avoid the problems of slow reconstruction as may occur when using CS reconstruction and/or avoid introducing false data into the image. An ultrasound imaging system that applies deep learning (e.g., generative model) to reconstruct high resolution images from undersampled data may allow for the ultrasound imaging system to realize one or more improvements in performance. For example, the ultrasound imaging system may utilize ultrasound probes with fewer transducer elements and/or utilize fewer channels from a transducer array. This may allow the ultrasound imaging system to include lower cost ultrasound probes, reduce hardware costs, and/or reduce amount of hardware in the ultrasound imaging system. Implementing the systems and methods described herein, an ultrasound imaging system may increase frame rate, reduce transmit events, reduce sampling rate, reduce artifacts from one or more sources (e.g., lobes, Gibbs ringing, off-axis noise, false data), improve lateral and/or axial resolution, and/or improve reconstruction speed. This may allow the ultrasound imaging system to provide high quality images with diagnostic value for real time or near real time imaging applications.

Figure 2:
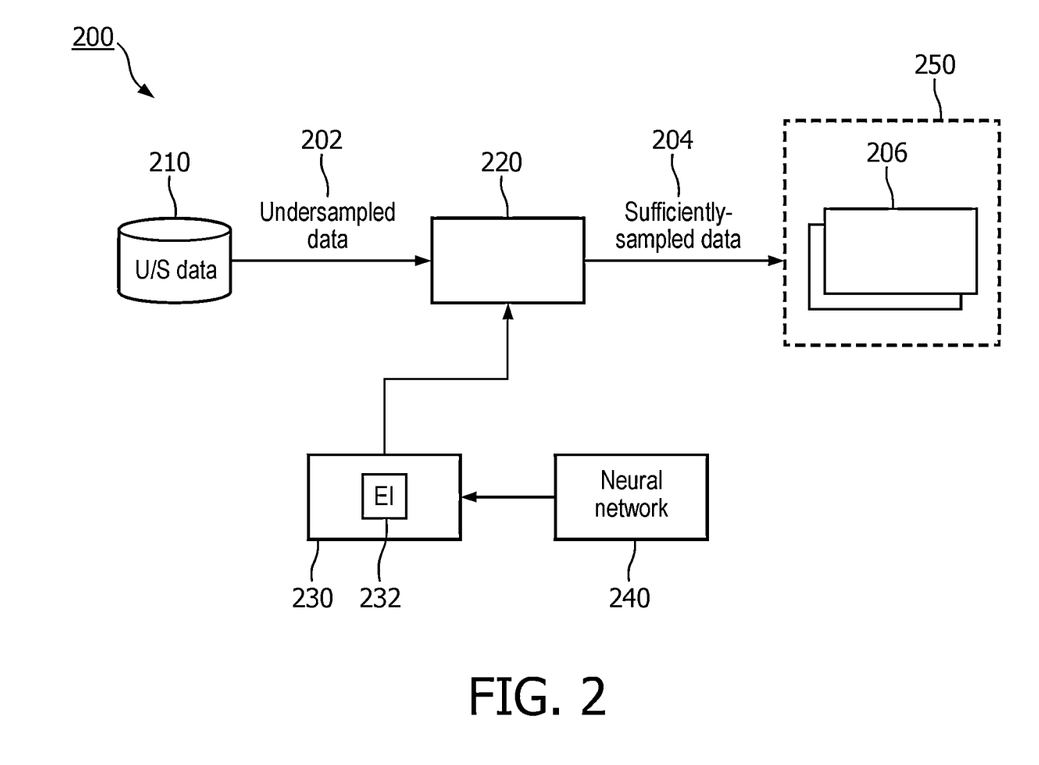
FIG. 2 is a block diagram of a system according to the principles of the present disclosure.

FIG. 2 shows a block diagram of a system for generating ultrasound images in accordance with the principles of the present disclosure. System 200 includes a storage device 210 and a processor 220 coupled to the storage device. The storage device 210 may include one or more hard disk drives, solid state drives, or any other type of non-volatile memory and may be co-located with the processor 220 (e.g., within the same machine, such as when system 200 is part of an ultrasound scanner) or remotely located (e.g., in a picture archiving and communication system (PACS) server), to which the processor 220 may be connected via a wired or wireless connection. The processor 220 may include a single or multi-core CPU, a single GPU or GPU cluster, or multiple processors arranged for parallel processing. The processor 220 may be programmed, by processor-executable instructions 232 stored on at least one non-transitory computer readable storage medium 230 coupled to the processor, to receive undersampled ultrasound data 202, modify, using a neural network 240, the undersampled ultrasound data to represent sufficiently-sampled ultrasound data 204, and generate an ultrasound image 206 based on the modified ultrasound data. In some embodiments, the system 200 may optionally include a display 250 for displaying the ultrasound images 206 and/or a user interface for operating system 200. In some embodiments, some or all of the components of system 200 may be integrated with an ultrasound imaging device. For example, the processor 220 may be incorporated in an ultrasound imaging system, an example of which is described with reference to FIG. 4. In some examples, the processor 220 may be incorporated into a non-imaging system (e.g., an analysis workstation) operable to produce images from ultrasound data. In some embodiments, the neural network 240 may implement at least a portion of a generative adversarial network (GAN) trained in accordance with the examples herein. For example, the neural network 240 may implement a trained generative classification model (or interchangeably, generative model or generative classifier) of a GAN, trained in accordance with the examples herein.

Figure 3:
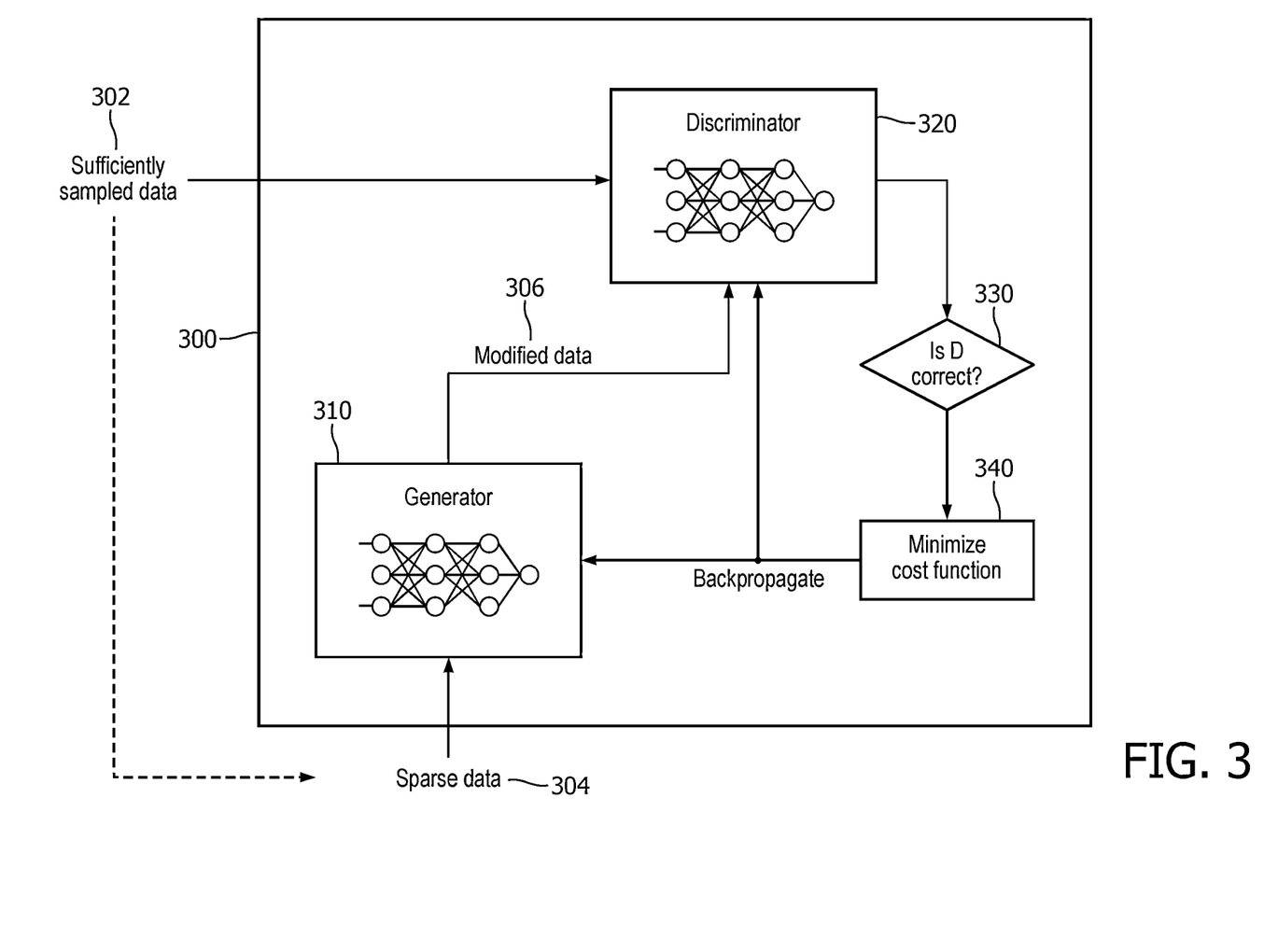
FIG. 3 is a block diagram of a generative adversarial network in accordance with the examples herein.

FIG. 3 shows an example of a GAN 300 implemented in accordance with the principles of the present invention. The GAN 300 includes a generator 310 and a discriminator 320. To train the network, GAN 300 receives, as inputs, a sufficiently-sampled dataset 302 and a sparse (or undersampled) dataset 304. The term sparse data or sparsely sampled data may imply that the dataset contains fewer than necessary samples to produce an accurate reconstruction of an continuous signal. Conversely, a sufficiently-sampled dataset is a dataset containing a sufficient number of samples to reduce error in reconstruction, e.g., sampling at or above the Nyquist frequency to remove error such as aliasing in the reconstructed signal. In operation, sparsely sampling a continuous signal may provide advantages (reduce the time the number of transducer elements and/or channels needed to measure the continuous signal). Thus, new and improved techniques for using sparsely sampled data to produce an accurate reconstruction of the sampled signal are desirable.

Returning back to FIG. 3, the sufficiently-sampled dataset 302 is a real dataset. That is, the sufficiently-sampled dataset 302 is a dataset from previously acquired medical image data and is therefore also referred to as acquired sufficiently-sampled dataset 302. The generator 310, as described further below, produces a modified dataset 306 (also referred to as generated sufficiently-sampled dataset) based on the sparse dataset 304, e.g., using the sparse dataset 304 to seed the generation of the modified dataset 306. In some examples, the acquired sufficiently-sampled dataset 302 may include ultrasound data obtained from ultrasound signals sampled at least at a rate equal to or greater than twice the highest frequency of the ultrasound signals. In some examples, the acquired sufficiently-sampled dataset 302 may include ultrasound data obtained from a frame rate greater than 40 Hz. In some examples, the acquired sufficiently-sampled dataset 302 may include ultrasound data packaged into a number of channels from an ultrasound probe to an ultrasound system, in which the number of channels is equal to or greater than a number of transducer elements. The terms sufficiently-sampled and fully sampled are interchangeably used herein. Moreover, the term acquired is meant to imply real data or data acquired through imaging, while the term generated are meant to imply data simulated or generated by the neural network.

For training purposes, the sparse dataset 304 is derived from an acquired sufficiently-sampled dataset 302, e.g., by removing samples from the fully sampled dataset 302. As such, the acquired sufficiently-sampled dataset 302 represents ground truth for any generated sufficiently-sampled dataset 306 output by generator 310 responsive to a corresponding sparse dataset 304.

The generator 310 includes a multilayered network of artificial neural nodes trained to do generate the data missing from the reduced samples dataset 304, which is combined with the reduced samples dataset 304 to produce a modified dataset 306. The modified dataset 306 includes the real image data (e.g., data from either the image space or the k-space) retained from the fully sampled dataset after the down sampling, and the image data produced by the generator to represent the missing data removed by the downsampling. The generator 310 may implement a generative classification model, which for a set of input data that classified into labels y, learns the joint probability distribution p(x,y), which can be used to generate likely (x,y) pairs for any set of unknown input data x. The discriminator 302 includes another multilayered network of artificial neural nodes trained to differentiate or discriminate between real (e.g., actual or correctly estimated) image data and fake (e.g., incorrectly estimated) image data. The generator and discriminator may include any number and type of layers including, but are not limited to, convolution layers and fully connected layers (e.g., Fast Fourier Transform layers, mathematical representation layers).

The discriminator 302 learns the conditional probability distribution p(y|x), that is, the probability of a label y (e.g., real or fake) given an input x. The generative and discriminative distribution functions of the generator 310 and discriminator 320, respectively, are simultaneously updated, e.g., by backpropagation or other optimization algorithm to minimize (as shown in block 340) the cost function or error computed at block 330. The distribution functions are updated until convergence, that is, until the generator 310 and discriminator 320 can no longer improve because the discriminator is no longer able to differentiate between the two distributions. Once sufficiently trained, the generator 310 may be implemented as a neural network integrated into or communicatively coupled to an ultrasound imaging system (e.g., an ultrasound scanner) or another a source of ultrasound image data (e.g., analysis workstation coupled to PACS) for generating images from unknown (e.g., newly acquired) undersampled ultrasound data.

Figure 4:
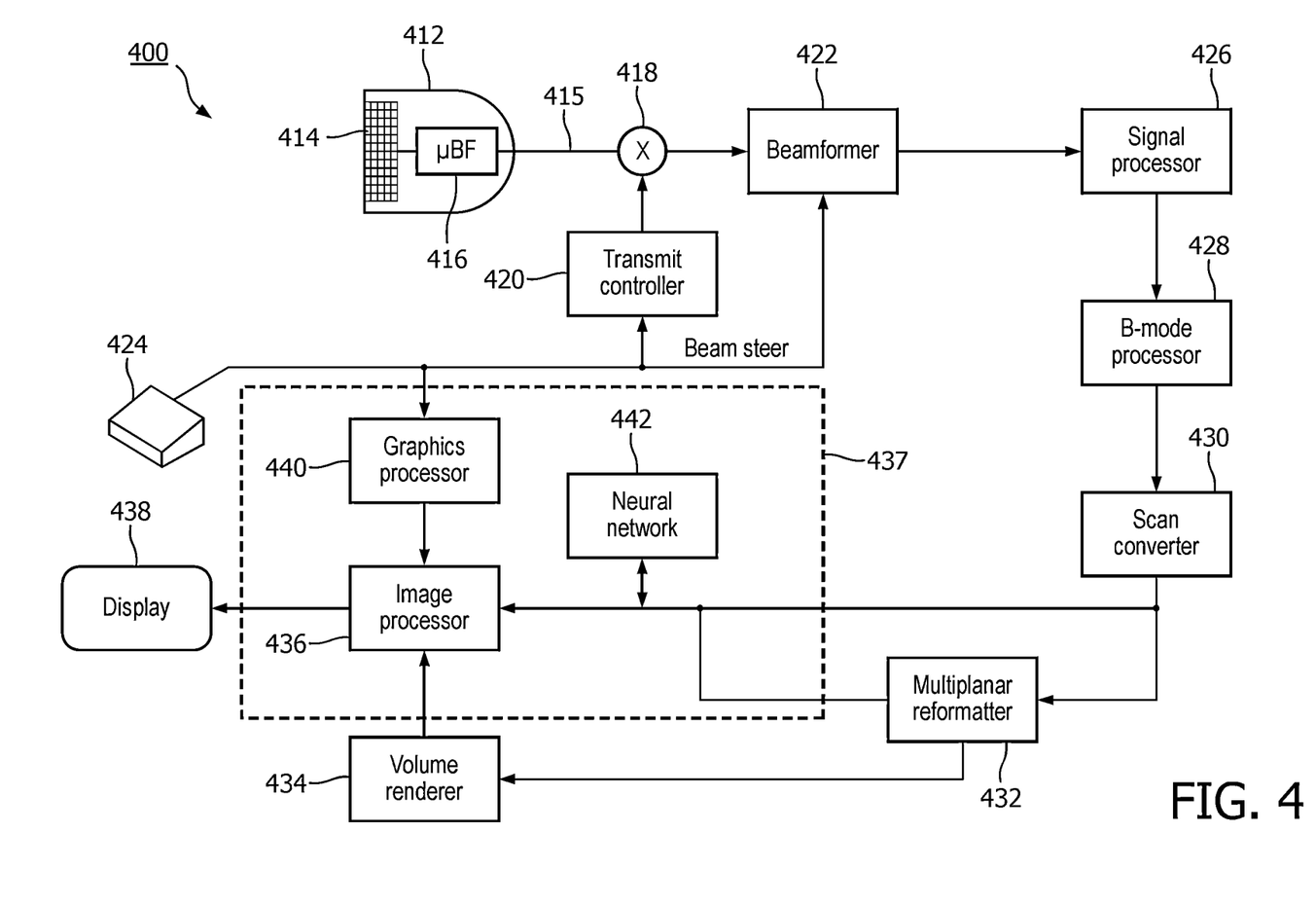
FIG. 4 is a block diagram of an ultrasound imaging system in accordance with the principles of the present disclosure.

FIG. 4 shows a block diagram of an ultrasound imaging system that applies a neural network to undersampled ultrasound data in accordance with the principles of the present invention. In the ultrasound imaging system 400 of FIG. 4, an ultrasound probe 412 includes a transducer array 414 for transmitting ultrasonic waves and receiving echo information. The transducer array 414 may be implemented as a linear array, convex array, a phased array, and/or a combination thereof. The transducer array 414, for example, can include a two dimensional array (as shown) of transducer elements capable of scanning in both elevation and azimuth dimensions for 2D and/or 3D imaging. The transducer array 414 may be coupled to a microbeamformer 416 in the probe 412, which controls transmission and reception of signals by the transducer elements in the array. In this example, the microbeamformer 416 is coupled by the probe cable to a transmit/receive (T/R) switch 418, which switches between transmission and reception and protects the main beamformer 422 from high energy transmit signals. In some embodiments, the T/R switch 418 and other elements in the system can be included in the ultrasound probe 412 rather than in a separate ultrasound system base. In some embodiments, the ultrasound probe 412 may be coupled to the ultrasound imaging system via a wireless connection (e.g., WiFi, Bluetooth).

The transmission of ultrasonic beams from the transducer array 414 under control of the microbeamformer 416 is directed by the transmit controller 420 coupled to the T/R switch 418 and the beamformer 422, which receives input from the user's operation of the user interface (e.g., control panel, touch screen, console) 424. The user interface may include soft and/or hard controls. One of the functions controlled by the transmit controller 420 is the direction in which beams are steered. Beams may be steered straight ahead from (orthogonal to) the transducer array, or at different angles for a wider field of view. The partially beamformed signals produced by the microbeamformer 416 are coupled via channels 415 to a main beamformer 422 where partially beamformed signals from individual patches of transducer elements are combined into a fully beamformed signal. In some embodiments, microbeamformer 416 is omitted and the transducer array 414 is coupled via channels 415 to the beamformer 322. In some embodiments, the system 400 may be configured (e.g., include a sufficient number of channels 415 and have a transmit/receive controller programmed to drive the array 414) to acquire ultrasound data responsive to a plane wave or diverging beams of ultrasound transmitted toward the subject. In some embodiments, the number of channels 415 from the ultrasound probe may be less than the number of transducer elements of the array 414 and the system may operable to acquire ultrasound data packaged into a smaller number of channels than the number of transducer elements.

The beamformed signals are coupled to a signal processor 426. The signal processor 426 can process the received echo signals in various ways, such as bandpass filtering, decimation, I and Q component separation, and harmonic signal separation. The signal processor 426 may also perform additional signal enhancement such as speckle reduction, signal compounding, and noise elimination. The processed signals are coupled to a B mode processor 428, which can employ amplitude detection for the imaging of structures in the body. The signals produced by the B mode processor are coupled to a scan converter 430 and a multiplanar reformatter 432. The scan converter 430 arranges the echo signals in the spatial relationship from which they were received in a desired image format. For instance, the scan converter 430 may arrange the echo signal into a two dimensional (2D) sector-shaped format, or a pyramidal three-dimensional (3D) image. The multiplanar reformatter 432 can convert echoes, which are received from points in a common plane in a volumetric region of the body into an ultrasonic image of that plane, as described in U.S. Pat. No. 6,443,896 (Detmer).

A volume renderer 434 converts the echo signals of a 3D data set into a projected 3D image as viewed from a given reference point, e.g., as described in U.S. Pat. No. 6,530,885 (Entrekin et al.) The 2D or 3D images may be coupled from the scan converter 430, multiplanar reformatter 432, and volume renderer 434 to at least one processor 437 for further image processing operations.

For example, the at least one processor 437 may include an image processor 436 configured to perform further enhancement and/or buffering and temporary storage of image data for display on an image display 438. The display 438 may include a display device implemented using a variety of known display technologies, such as LCD, LED, OLED, or plasma display technology. The at least one processor 437 may include a graphics processor 440 which can generate graphic overlays for display with the ultrasound images. These graphic overlays can contain, e.g., standard identifying information such as patient name, date and time of the image, imaging parameters, and the like. For these purposes the graphics processor 440 receives input from the user interface 424, such as a typed patient name. The user interface 424 can also be coupled to the multiplanar reformatter 432 for selection and control of a display of multiple multiplanar reformatted (MPR) images. The user interface 424 may include one or more mechanical controls, such as buttons, dials, a trackball, a physical keyboard, and others, which may also be referred to herein as hard controls. Alternatively or additionally, the user interface 424 may include one or more soft controls, such as buttons, menus, soft keyboard, and other user interface control elements implemented for example using touch-sensitive technology (e.g., resistive, capacitive, or optical touch screens). One or more of the user controls may be co-located on a control panel. For example one or more of the mechanical controls may be provided on a console and/or one or more soft controls may be co-located on a touch screen, which may be attached to or integral with the console.

The at least one processor 437 may also perform the functions associated with producing images from undersampled data, as described herein. For example, the processor 437 may include or be operatively coupled to a neural network 442. The neural network 442 may implement at least one multilayer network of artificial neural nodes which are trained to generate ultrasound images representative of fully sampled images from undersampled ultrasound data. For example, the neural network 442 may include a multilayer network of artificial neural nodes implementing a generative machine learning model trained in accordance with the examples herein, e.g., as described with reference to FIG. 3. Although described as separate processors, it will be understood that the functionality of any of the processors described herein (e.g., processors 436, 440, 442) may be implemented in a single processor (e.g., a CPU or GPU implementing the functionality of processor 437) or fewer number of processors than described in this example. In yet other examples, the neural network 442 may be hardware-based (e.g., include multiple layers of interconnected nodes implemented in hardware) and be communicatively connected to the processor 437 to output to processor 437 the requisite image data for generating ultrasound images. While in the illustrated embodiment, the neural network is implemented in parallel and/or conjunction with the image processor 436, in some embodiments, the neural network 442 may be implemented at other processing stages, e.g., prior to the processing performed by the image processor 436, volume renderer 434, multiplanar reformatter 432, and/or scan converter 430. In some embodiments, the neural network 442 may be implemented to process ultrasound data in the channel domain, beamspace domain (e.g., before or after beamformer 422), the IQ domain (e.g., before, after, or in conjunction with signal processor 426), and/or the k-space domain. As described, in some embodiments, functionality of two or more of the processing components (e.g., beamformer 422, signal processor 426, B-mode processor 428, scan converter 430, multiplanar reformatter 432, volume renderer 434, processor 437, image processor 436, graphics processor 440, etc.) may be combined into a single processing unit or divided between multiple processing units. The processing units may be implemented in software, hardware, or a combination thereof. For example, neural network 442 may include one or more graphical processing units (GPU). In another example, beamformer 422 may include an application specific integrated circuit (ASIC). Applying a properly trained neural network (e.g., a GAN) to sparsely sampled data for producing an image representative of sufficiently-sampled data may be achieved as described herein, as the neural network may learn, during the training process, a dictionary/transformation to be used during image generation and/or penalize for deviations from a deep learning model learned, a priori expectation of structure, or image characteristic.

Figure 5:
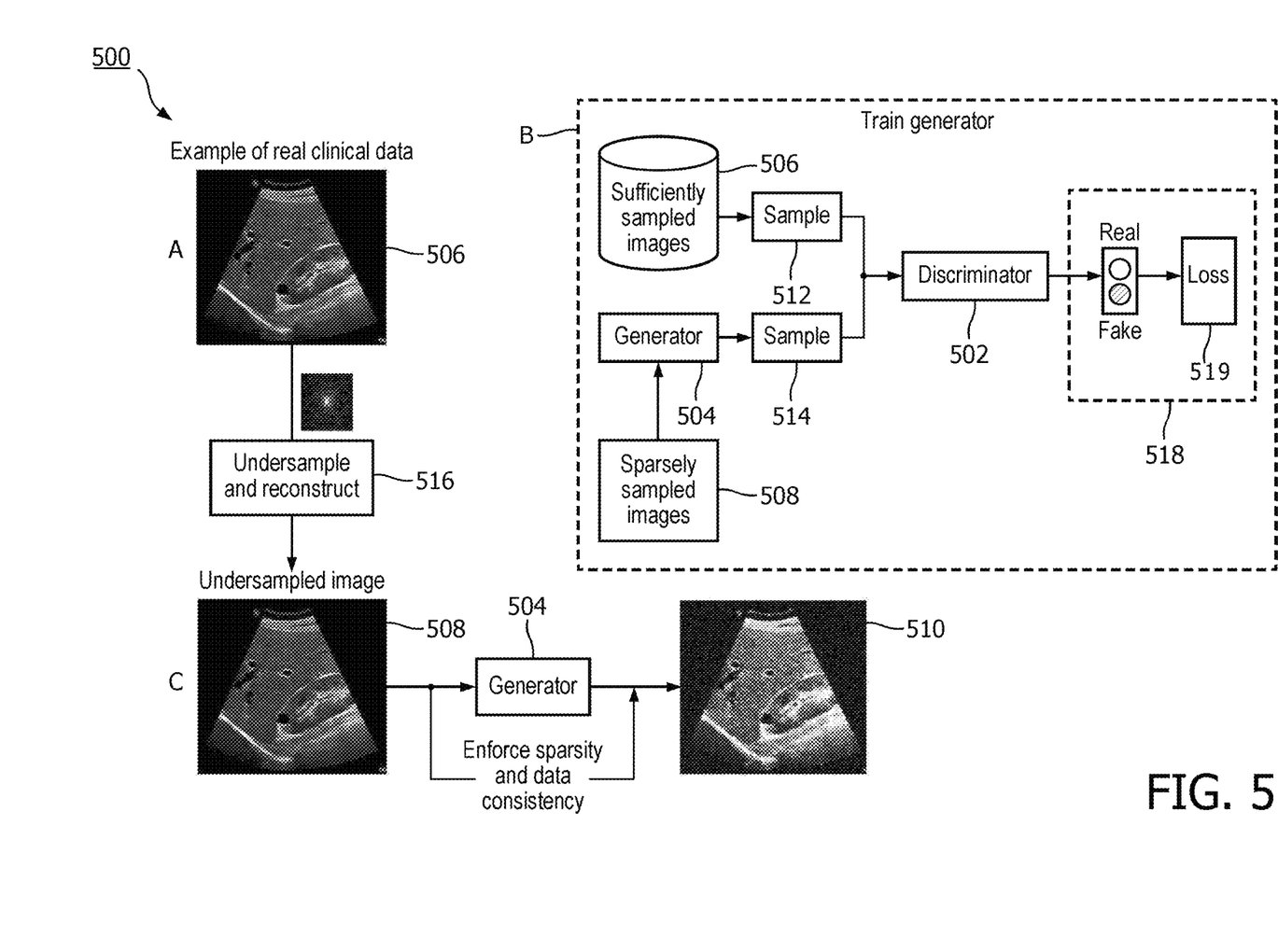
FIG. 5 illustrates an example of a training process for training a neural network according to the present disclosure.

An example training environment and process are described further with reference to FIG. 5. As shown in FIG. 5, a deep generative network (DGN) such as a GAN may be implemented (e.g., in software) and trained using real clinical images. With the increasing volume of stored medical imaging data (e.g., in PACS or in cloud storage), the availability of high-quality clinical image data is increasing, which may be leveraged to train neural networks for a variety of purposes including for producing higher resolution (spatial or temporal) images from an acquired lower resolution dataset and/or more efficiently than with existing/conventional techniques. As shown in FIG. 5, the GAN may include a first neural network implementing a generative model or generator 504 and a second neural network implementing a discriminative model or discriminator 502. In the example training process 500, the process may start by retrieving a plurality of previously-acquired ultrasound images (e.g., example image 506). The previously-acquired images 506 contain sufficiently-sampled ultrasound data. As shown in block 516, the previously-acquired ultrasound image data is downsampled. That is, sampling of the previously-acquired ultrasound image data is reduced to produce a plurality of corresponding sparsely sampled images (e.g., sparsely sampled image 508). As described herein, the sparsely sampled images used to train the neural network 504 are derived based on actual acquired image data rather than on random sparse data (e.g., using a random variable to seed image data generation) as is the case with existing GANs. This aspect of the described training process may reduce incoherent aliasing that is generally associated with existing GANs among other advantages that may be obtained from the current examples.

Pairs of corresponding sufficiently-sampled and under-sampled images are provided to the neural network for training, as shown in block B of FIG. 5. The training process 500 trains the generator 504 to produce sufficiently-sampled images (e.g., image 510) that would be indistinguishable from real/acquired images, and simultaneously trains the discriminator 502 to differentiate or distinguish between the generated sufficiently-sampled images 510 and the acquired sufficiently-sampled images 506. This is illustrated also in block B, which shows a sparsely sampled image 508 derived from the acquired sufficiently-sampled images 506 being coupled to generator 504 to produce the generated sufficiently-sampled images 510. Block B also shows samples 512 associated with the acquired sufficiently-sampled images and sample 514 associated with the generated sufficiently-sampled images 510 being provided as input to the discriminator 502, which classifies the samples as either real (e.g., representative of real/acquired image data) or fake (not corresponding to real image data), as shown in block 518. An error signal (e.g., loss of cost function 519) is computed based on the accuracy of the determination with respect to sample 514 in view of the real sample 512. The activation rules for one or more of the nodes of the discriminator and generator are then updated in a manner aimed to reduce the error signal. For example, backpropagation or other optimization algorithm is used to update the activation or transfer function of at least one node of the neural networks 502 and 504 in order to minimize the cost function at block 518. The goal of the training process is to continuously and simultaneously improve the performance of both the generator and discrimination towards convergence, such that the discriminator gets better and better at classifying the data as real or fake and the generator gets better and better at generating image data, until convergence—that is, until the discriminator can no longer differentiate an input as real or fake. The training process may thus continue until the generator is able to fool discriminator, that is, until the discriminator is unable to distinguish between real and fake data, at which point the trained generative model of generator 504 can be implemented (e.g., in executable instructions) as a neural network (e.g., 442) in a real ultrasound imaging or visualization system. In some embodiments, both the trained generator and discriminator may be implemented in the real system such that the adversarial generative network of the system may be further trained in the field (e.g., using image data acquired by the imaging system in which the adversarial network is deployed for training data).

As described herein, a neural network (e.g., a generative model) may be trained in accordance with the examples herein to generate higher quality (e.g., higher resolution, higher contrast, higher frame rate) ultrasound images from undersampled (e.g., sparse) ultrasound data. In some embodiments, a neural network trained an applied by an ultrasound system according to the examples herein may be used for frame rate improvement. For example, the neural network may be used to increase the frame rate of images produced by the ultrasound system as compared to the frame rate at acquisition, which may be advantageous in that it can reduce the number of transmit events required to generate an image and thus enhance real-time acquisition and display of images. The signals on which the neural network operates to fill in with generated samples may be from any domain of the acquired signals or at any stage of signal processing, for example the radio frequency (RF) domain or space, the temporal Fourier space, k space, or the image space.

Figure 6:
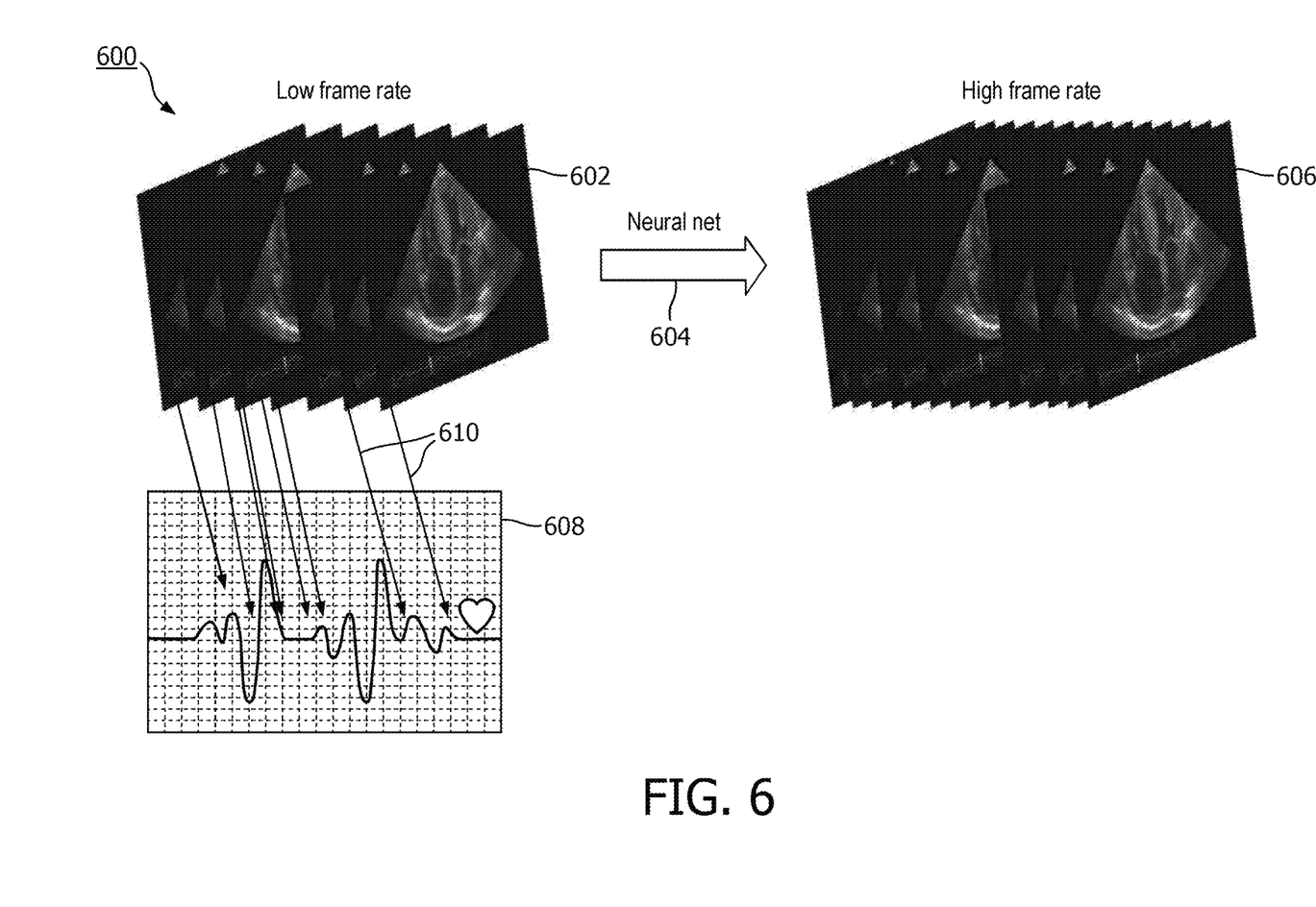
FIG. 6 illustrates an example of a system including a neural network operable to increase image frame rate in cardiac imaging according to the principles of the present disclosure.
Figure 7:
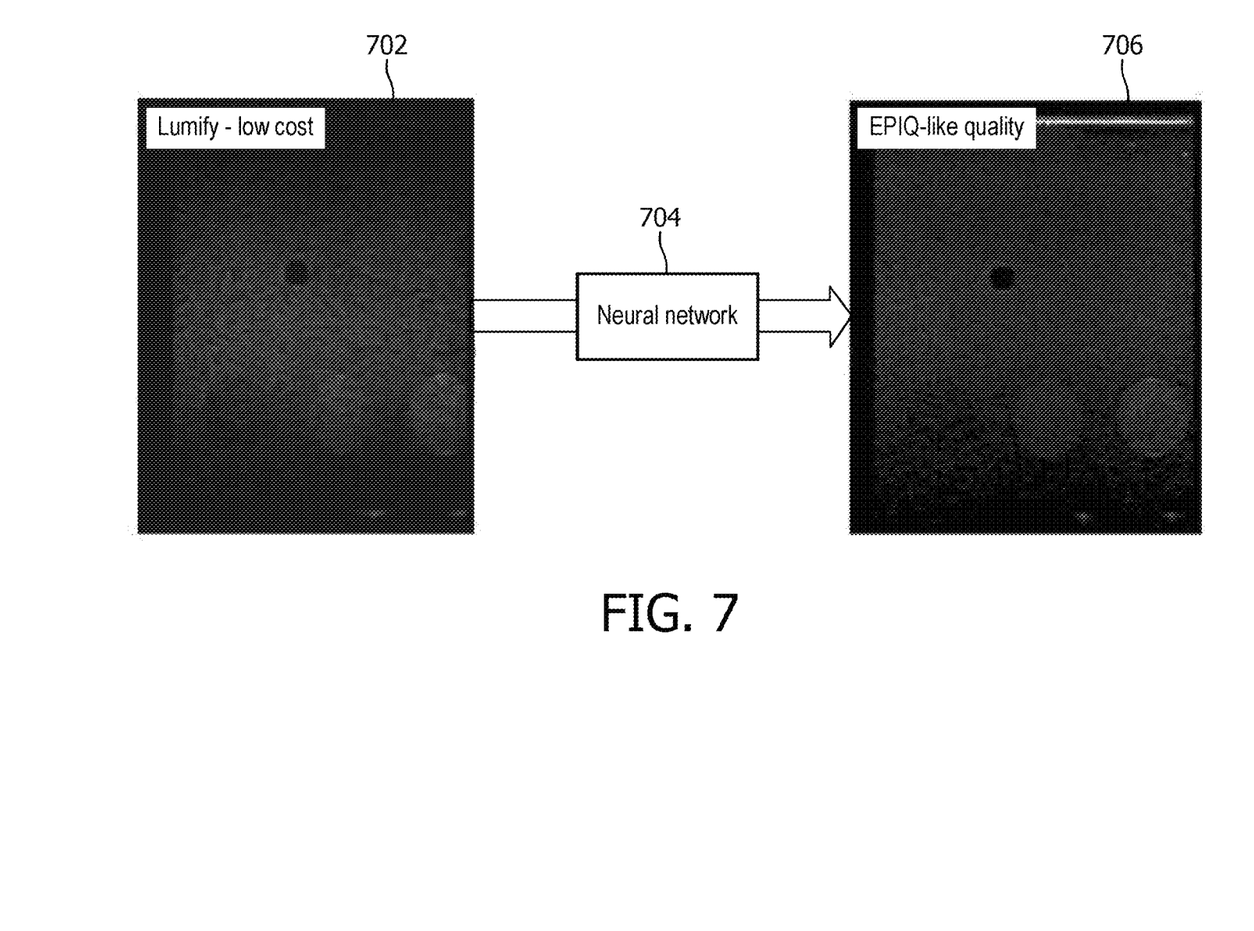
FIG. 7 illustrates an example of applying a neural network according to the examples herein to improve resolution.

In one embodiment related to frame rate improvement, a neural network according to the examples herein may be used to increase the frame rate in cardiac imaging. For example, as shown in FIG. 6, under sampled data 602 (e.g., ultrasound images acquired at a first frame) is provided to the neural network 604 of the system 600. The system 600 may be an ultrasound imaging system and thus include components for acquiring and processing ultrasound signals (e.g., some or all of the components of system 600). The system 600 may also be configured (e.g., with appropriate EKG leads, which may include one or more EKG input channels connected to one or more electrodes) to receive an electrocardiography (EKG) signal 608 and to acquire the images 602 at a frame rate based on the EKG signal 608. For example, the electrocardiography signal 608 may be used to trigger transmits by the system 600 at certain points in the cardiac cycle, e.g., as shown by arrows 610. As such, individual frames of the undersampled image data 602 may be associated with the specific points in the cardiac cycle, which may allow the system 600 to acquire real data at desired times during the cycle. The system may then fill, using the neural network 604, frames at other points in the cycle (i.e., one or more frames between one or more of the acquired frames) to produce ultrasound image frames 606 at a rate higher than the acquisition frame rate. EKG gating may also provide a method of non-uniformly sampling the data if a non-uniform sampling scheme is desired. For example, more ultrasound images may be acquired during the QRS complex rather than the P and T waves. In another example, ultrasound image acquisition and/or sampling may be timed to avoid sampling at the same points in the cardiac cycle each time.

Figure 8:
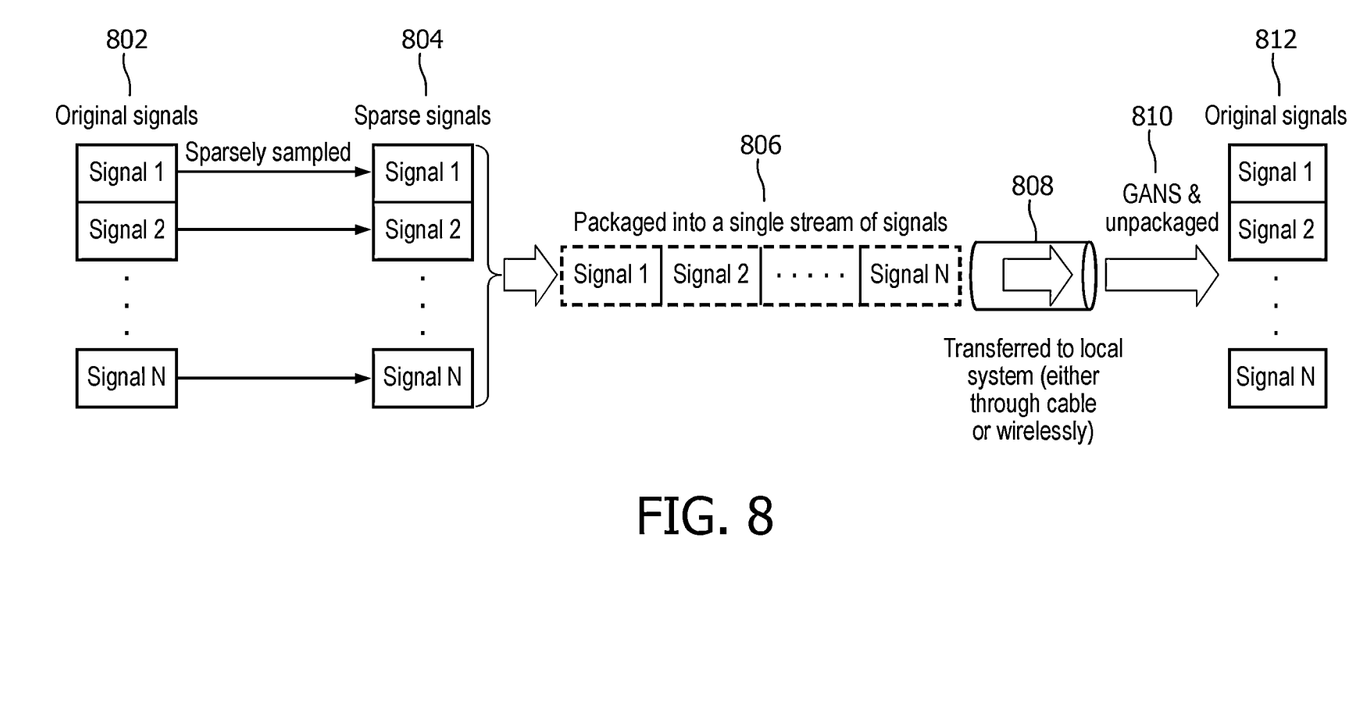
FIG. 8 illustrates an example of using a neural network to reduce the number of channels in an ultrasound imaging system according to principles of the present disclosure.

In some embodiments, an ultrasound system applying a neural network in accordance with the examples herein may be configured to improve the image resolution image data acquired with a lower cost imaging system, or may be used to reduce hardware requirements while still producing high quality images such as by enabling a system to be built with a smaller number of transducer elements and/or channels than standard higher quality systems. FIG. 8 illustrates an example of image quality improvement achieved using a system applying a neural network according to principles of the present disclosure. Image 702 is an ultrasound image acquired by a lower cost ultrasound imaging system (e.g., LUMIFY system by PHILIPS ULTRASOUND). The image 702 is coupled to a neural network 704 for generating image 706, which may be equivalent in quality to an image acquired natively by a higher cost ultrasound imaging system (e.g., EPIQ system provided by PHILIPS ULTRASOUND).

FIG. 8 illustrates another example of applying a neural network trained in accordance with the principles of the present disclosure. As shown in FIG. 8, original signals 802 (e.g., time continuous echo signals generated responsive to ultrasound pulses) may be measured by sparsely sampling the signals 802 to produce corresponding sparse signals 804. The sparse signals 804, e.g., acquired by a transducer array (e.g., array 414) may be packaged a single stream of data 806 and transmitted via a single channel 808 either through a cable or wirelessly. In the illustrated example, the signals 804 from different transducer elements are transmitted in serial via the single channel 808 rather than in parallel via separate channels, each of which may couple each transducer element to the signal processing system. Alternatively, the sparse signals 804 may be packaged into more than one stream of data and transmitted via corresponding number of channels to the system for processing, which number of data streams and channels may be fewer than the number of elements of the acquiring array. When received by the signal processing system, the sparse signals 806 may be coupled to a trained neural network (e.g., a trained generative classification model of an GAN) as illustrated by arrow 810. The trained neural network may then "unpackage" or fill-in the data missing from the sparse dataset to output a sufficiently sampled set of data 812 simulate to equate to the original signals 802.

Although examples of producing medical images from sparsely sampled data are described herein with reference to ultrasound image data, it will be understood that the examples herein are equally applicable to training a neural network to produce images from a sparse dataset of any imaging modality, such as magnetic resonance imaging (MRI), computed tomography (CT), positron emission tomography (PET), and virtually any other imaging modality.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A system for generating medical images, the system comprising:
    at least one storage device;
    at least one processor operatively coupled to the storage device; and
    at least one non-transitory computer readable storage medium storing instructions thereon, that, when executed by the at least one processor, cause the processor to:
    receive undersampled imaging data corresponding to images acquired during cardiac imaging;
    produce modified imaging data by modifying, using a neural network, the undersampled imaging data to represent sufficiently-sampled imaging data, the neural network trained by:
        providing a first data set comprising sufficiently-sampled imaging data corresponding to previously-acquired cardiac images;
        producing a second data set with missing data by reducing spatial and temporal sampling of the first data set to mimic undersampling caused by low frame rate acquisition as applied to the cardiac imaging over at least one cardiac cycle;
        coupling the second data set to one or more neural networks including the neural network to generate new data estimated to represent the missing data;
        producing a third data set by modifying the second data set to include the new data;
        classifying, by the one or more neural networks, the third data set as either real or fake; and
        adjusting activation rules for one or more nodes of the one or more neural networks based on an accuracy of the classifying; and
    generate a medical image based on the modified data.

2. The system of claim 1, wherein undersampled imaging data comprises imaging data obtained from signals sampled at a rate less than twice the highest frequency of signals from the sufficiently-sampled imaging data.

3. The system of claim 1, wherein undersampled imaging data comprises imaging data obtained from one or more magnetic resonance imaging (MRI), computed tomography (CT), and positron emission tomography (PET).

4. The system of claim 1, wherein the received undersampled imaging data is received at a frame rate of 40 Hz or less.

5. The system of claim 1, wherein the sufficiently-sampled imaging data comprises imaging data selected from a group consisting of:
    imaging data obtained from signals sampled at least a rate equal to or greater than twice the highest frequency of the signals from the undersampled imaging data; and
    imaging data obtained from a frame rate greater than 40 Hz.

6. The system of claim 1, wherein the undersampled imaging data, the modified data, or any of the first, second or third data sets comprise imaging data from an image space or a k-space.

7. The system of claim 1, wherein the neural network comprises at least a portion of a generative adversarial network.

8. The system of claim 7, wherein the neural network comprises a trained generative model of a generative adversarial neural network.

9. The system of claim 8, wherein the generative adversarial neural network further comprises a discriminative model, and wherein the generative and discriminative models are simultaneously trained by:
receiving a plurality of previously-acquired images, each comprising an acquired sufficiently-sampled dataset;
reducing sampling of each of the sufficiently-sampled datasets to produce respective generated sparse datasets;
training the neural network using training data comprising pairs of acquired sufficiently-sampled and corresponding generated sparse datasets, wherein the training includes:
coupling the generated sparse dataset of each pair to the generative model to produce a generated sufficiently-sampled dataset;
coupling the acquired sufficiently-sampled and the generated sufficiently-sampled dataset of each pair to the discriminative model to classify the generated sufficiently-sampled dataset as real or fake and to compute an error signal representative of accuracy of the classification; and
adjusting one or more activation functions for respective one or more nodes of the discriminative model and the generative model, wherein the adjusting is configured to reduce the error signal.

10. A method of generating medical images from sparsely sampled imaging data, the method comprising:
receiving undersampled imaging data corresponding to images acquired during cardiac imaging;
coupling the undersampled imaging data to a neural network to produce modified imaging data representative of sufficiently-sampled imaging data, the neural network is trained by:
providing a first data set comprising sufficiently-sampled imaging data corresponding to previously-acquired cardiac images;
producing a second data set with missing data by reducing spatial and temporal sampling of the first data set to mimic undersampling caused by low frame rate acquisition as applied to the cardiac imaging over at least one cardiac cycle;
coupling the second data set to one or more neural networks including the neural network to generate new data estimated to represent the missing data;
producing a third data set by modifying the second data set to include the new data;
classifying, by the one or more neural networks, the third data set as either real or fake; and
adjusting activation rules for one or more nodes of the one or more neural networks based on an accuracy of the classification; and
generating one or more medical images based on the modified data.

11. The method of claim 10, wherein the receiving undersampled imaging data comprises acquiring signals by sampling an imaging signal at a rate less than twice the highest frequency of the imaging signal.

12. The method of claim 10, wherein the receiving undersampled imaging data comprises acquiring imaging signals from a medium responsive to one or more of magnetic resonance imaging (MRI), computed tomography (CT), and positron emission tomography (PET).

13. The method of claim 10, wherein the receiving undersampled imaging data comprises acquiring images at a frame rate of 40 Hz or less.

14. The method of claim 10, wherein the sufficiently-sampled imaging data comprises imaging data selected from a group consisting of:
imaging data obtained from signals sampled at least a rate equal to or greater than twice the highest frequency of the signals from the undersampled imaging data; and
imaging data obtained from a frame rate greater than 40 Hz.

15. The method of claim 10, wherein the coupling the undersampled imaging data to a neural network comprises coupling the undersampled imaging data to a trained generative model of a generative adversarial neural network comprising a generative model and a discriminative model, and wherein the generative model is trained by:
retrieving a plurality of previously-acquired medical images, each comprising an acquired sufficiently-sampled dataset;
reducing sampling of each of the sufficiently-sampled datasets to produce respective generated sparse datasets;
training the neural network using training data comprising pairs of acquired sufficiently-sampled and corresponding generated sparse datasets, wherein the training includes:
coupling the generated sparse dataset of each pair to the generative model to produce a generated sufficiently-sampled dataset;
coupling the acquired sufficiently-sampled and the generated sufficiently-sampled dataset of each pair to the discriminative model to classify the generated sufficiently-sampled dataset as real or fake and to compute an error signal representative of accuracy of the classification; and
adjusting one or more activation functions for respective one or more nodes of the discriminative model and the generative model, wherein the adjusting is configured to reduce the error signal.

16. The method of claim 15, wherein the generative model of the generative adversarial neural network is considered a trained generative model when the discriminator is incapable of differentiating between the acquired sufficiently-sampled dataset and the generated sufficiently-sampled dataset.

17. The method of claim 10, further comprising receiving an EKG signal, acquiring the undersampled imaging dataset at a frame rate based on the EKG signal, wherein the generating one or more medical images comprises generating image frames at a rate higher than the frame rate.

18. A non-transitory computer-readable medium comprising executable instructions, which when executed cause a processor of a medical imaging system to perform the steps of:
receiving undersampled imaging data corresponding to images acquired during cardiac imaging;
coupling the undersampled imaging data to a neural network to produce modified imaging data representative of sufficiently-sampled imaging data, the neural network is trained by:
providing a first data set comprising sufficiently-sampled imaging data corresponding to previously-acquired cardiac images;

producing a second data set with missing data by reducing spatial and temporal sampling of the first data set to mimic undersampling caused by low frame rate acquisition as applied to the cardiac imaging over at least one cardiac cycle;

coupling the second data set to one or more neural networks including the neural network to generate new data estimated to represent the missing data;

producing a third data set by modifying the second data set to include the new data;

classifying, by the one or more neural networks, the third data set as either real or fake; and adjusting activation rules for one or more nodes of the one or more neural networks based on an accuracy of the classification; and generating one or more medical images based on the modified data.

\* \* \* \* \*